US00PP11186P

United States Patent [19]

Kordes

[11] Patent Number: Plant 11,186

[45] Date of Patent: Jan. 25, 2000

[54] MINIATURE ROSE PLANT NAMED 'KORTRON'

[75] Inventor: Wilhelm Kordes, Sparrieshoop, Germany

[73] Assignee: Bear Creek Gardens, Inc., Medford, Oreg.

[21] Appl. No.: 09/073,077

[22] Filed: May 4, 1998

[51] Int. Cl.[7] ..... A01H 5/00

[52] U.S. Cl. ..... Plt./121

[58] Field of Search ..... Plt./116, 120, 121, Plt./123, 127, 128

*Primary Examiner*—Howard J. Locker

*Attorney, Agent, or Firm*—Klarquist, Sparkman, Campbell, Leigh & Whinston, LLP

[57] ABSTRACT

Miniature rose plant having a compact, well branched plant habit; ease of rooting from softwood cuttings; free flowering; long lasting flower color; and good shelf life.

1 Drawing Sheet

The present invention relates to a new and distinct variety of rose plant of the miniature class which was originated by me by crossing an unnamed, unpatented seedling of a cross of varieties 'INTERmoto'×'KORgiffer', with the variety 'KORcelin' (unpatented).

The primary objective of this breeding was to produce a new miniature rose variety having a compact, well branched plant habit; ease of rooting from softwood cuttings; free flowering; long lasting flower color; and good shelf life. The objective was substantially achieved, along with other desirable improvements, as evidenced by the following unique combination of characteristics that are outstanding in the new variety and that distinguish it from its parents, as well as from all other varieties of which I am aware:

1. Compact, well branched growth habit;
2. Good shelf life;
3. Long lasting, stable flower color;
4. Easy, reliable rooting from softwood cuttings;
5. Free flowering.

'KORtron' was bred, selected, and tested for its adaptation to pot rose culture. It makes an ideal pot rose grown in a 10 cm. pot. Its fast growth and excellent shelf life combined with attractive flowers makes it an excellent variety for greenhouse culture and sale as a flowering pot plant.

Asexual reproduction of this new variety by cutting propagation, as performed at Sparrieshoop, Germany, and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'INTERmoto'×'KORgiffer' (unpatented).

*Pollen parent.*—'KORcelin' (unpatented).

Classification:

*Botanical.*—Rosa hybrida.

*Commercial.*—Miniature rose.

FLOWER

Observations made from specimens grown in a greenhouse environment at Sparrieshoop, Germany and at Somis, Calif. from March, 1997 to February, 1998.

Blooming habit: Continuous.

Bud:

*Size.*—Three-quarters inch long when the petals start to unfurl.

*Form.*—The bud form is long, pointed ovoid.

*Color.*—When sepals first divide, bud color is Red Group 48C. When half blown, the upper sides of the outer petals are Red Group 48C; the inner petals are Red Group 48C on the outer one-third of the petal, Red Group 40D on the middle one-third, and Yellow-Orange Group 15C on the inner one-third of the petals; and the lower sides of the petals are all Red Group 48C.

*Sepals.*—Color: Green group 137D. Surface texture: Covered in fine hairs. There are three lightly appendaged sepals. There are two unappendaged sepals with hairy edges.

*Receptacle.*—Color: Green Group 137D. Shape: Funnel. Size: Small (¼"×¼"). Surface: Smooth.

*Peduncle.*—Length: Short (¾"). Surface: Smooth. Color: Yellow-Green Group 146C. Strength: Stiff, erect.

Bloom:

*Size.*—Small. Average open size is 1¾ inches.

*Borne.*—Singly.

*Stems.*—Short, strong. Average length is about five inches.

*Form.*—When first open: High centered. Permanence: Flattens, outer petals curl back.

*Petalage.*—Number of petals under normal conditions: 25–30.

*Color.*—The upper sides of the outer petals are Red Group 48C; the inner petals are Red Group 48C on the outer one-third of the petals, Red Group 40D on the middle one-third of the petals, and Yellow-Orange Group 15C on the inner one-third of the petals. The reverse sides of the petals are Red Group 48C. The base of each petal has a small (1/16"×⅛"), Yellow Group 13A, half moon at the point of attachment. The major color on the upper sides is Red Group 48C.

*Variegations.*—Occasional greenish-white streak on the guard petals.

*Discoloration.*—At the end of the first day: No change. At the end of the third day: No change. As the flower opens on the plant, there is no change through day nine or ten. From day ten to petal drop at day fifteen to day eighteen the petals in the center of the flower fade to Red Group 43C.

*Fragrance.*—None.

Petals:

*Texture.*—Leathery.

*Shape.*—Round to deltoid.

*Form.*—Tips slightly recurved, edges slightly quilled.

*Arrangement.*—Imbricated. Petaloids in the center are few and small.

*Persistence.*—Petals drop off cleanly before drying.

*Lastingness.*—On the plant: Very long (fifteen to eighteen days). As a cut flower: Very long (about twenty-one days).

Reproductive parts:

*Anthers.*—Size: Medium. Quantity: Many. Color: Yellow. Arrangement: Regular around styles mixed with a few petaloids.

*Filaments.*—Color: Yellow.

*Pollen.*—Color: Gold yellow.

*Styles.*—Color: Greenish-white.

*Stigmas.*—Color: Greenish-White.

Plant:

*Form.*—Bush.

*Growth.*—Vigorous; upright; branching; compact. At maturity in a garden setting, height is eighteen to twenty inches tall, width is fourteen to sixteen inches. When grown as a pot rose in a 10 cm pot, the plant is eight inches in height and eight inches wide.

Foliage: Number of leaflets on normal midstem leaves: Five.

*Size.*—Small (2⅓" long×1¾"-2" wide).

*Quantity.*—Abundant.

*Color.*—New foliage: Upper and lower surfaces: Greyed-Red Group 178A. Old foliage: Upper surface: Green Group 137A. Lower surface: Green Group 139C.

*Shape.*—Pointed oval.

*Texture.*—Upper side: Leathery, glossy.

*Edge.*—Serrated.

*Serration.*—Single, small.

*Petiole rachis.*—Color: Greyed-Purple Group 183B on upper surface, Green Group 139C on lower surface.

*Petiole underside.*—Smooth with occasional prickles.

*Stipules.*—Short (⅜"), serrated.

*Disease resistance.*—Resistant to mildew under normal growing conditions in the greenhouse at Sparrieshoop, Germany and Somis, Calif.

Wood:

*New wood.*—Color: Greyed-Red Group 178A. Bark: Smooth.

*Old wood.*—Color: Green Group 137C. Bark: Smooth.

Prickles:

*Quantity.*—On main canes from base: Few. On laterals from main canes: Few.

*Form.*—Short, straight.

*Color when young.*—Green.

Small prickles:

*Quantity.*—On main stalks: None. On laterals: None.

I claim:

1. A new and distinct variety of miniature rose plant as herein shown and described characterized particularly by a compact, well branched plant habit; ease of rooting from softwood cuttings; free flowering; long lasting flower color; and good shelf life.

* * * * *

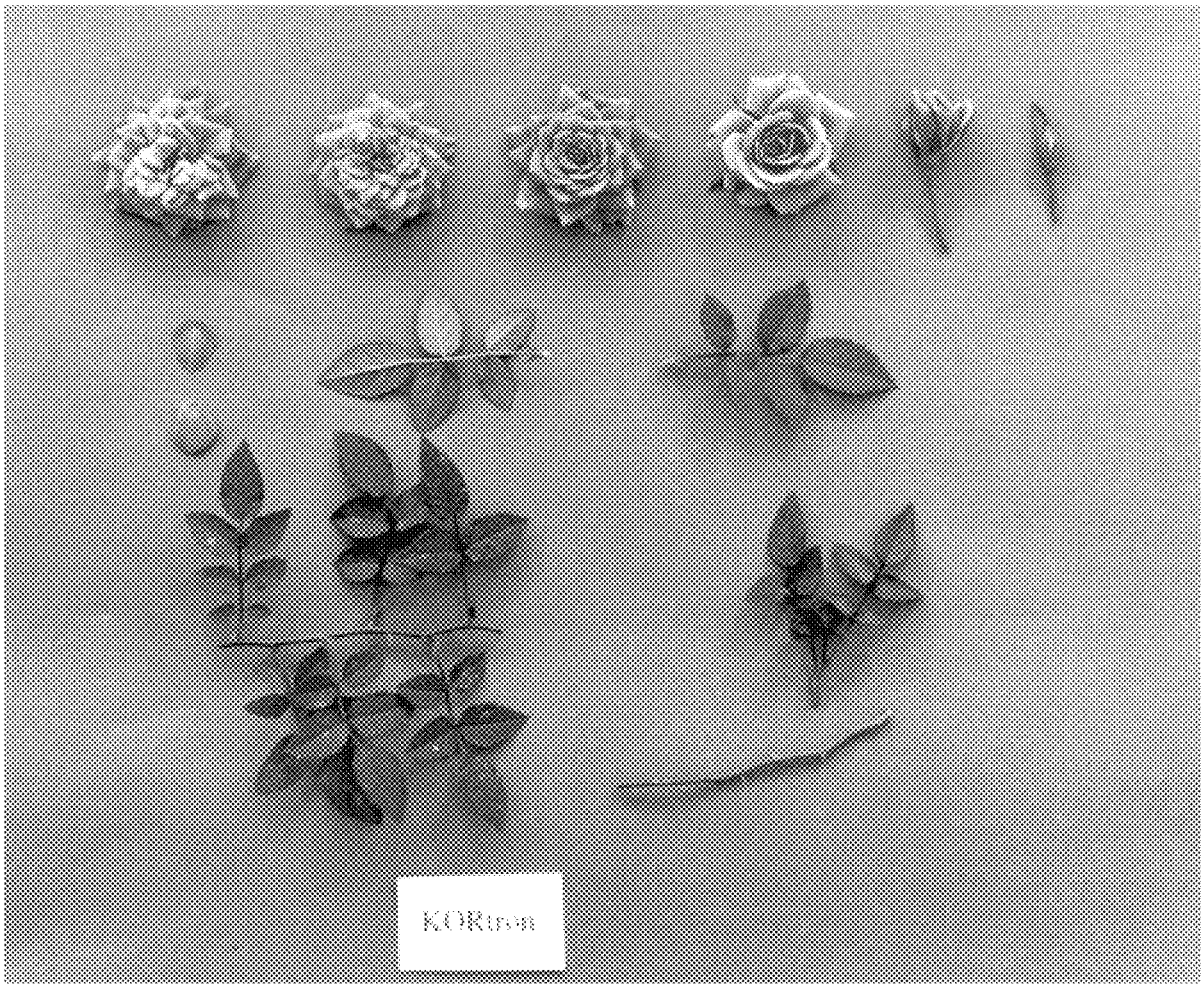
KORison